United States Patent [19]

Rothman et al.

[11] 4,115,536

[45] Sep. 19, 1978

[54] AGENT FOR INTRAVASCULAR ADMINISTRATION

[75] Inventors: Ulf Sven Erik Rothman, Höllviksnäs; Sven Lennart Kägedal; John Lennart Söderberg, both of Upsala, all of Sweden

[73] Assignee: Pharmacia Fine Chemicals AB, Upsala, Sweden

[21] Appl. No.: 611,942

[22] Filed: Sep. 10, 1975

[30] Foreign Application Priority Data

Sep. 27, 1974 [SE] Sweden ................................. 7412164

[51] Int. Cl.$^2$ ...................... A61K 29/00; A61K 43/00
[52] U.S. Cl. ........................................ 424/1; 252/408; 424/9
[58] Field of Search .................. 252/424, 264, 408

[56] References Cited

U.S. PATENT DOCUMENTS

| 3,663,685 | 5/1972 | Evans | 424/1 |
| 3,758,678 | 9/1973 | Lindsay et al. | 424/1 |
| 3,853,987 | 12/1974 | Dreyer | 424/1 |

Primary Examiner—Benjamin R. Padgett
Assistant Examiner—Christine M. Nucker
Attorney, Agent, or Firm—Fred Philpitt

[57] ABSTRACT

The present invention relates to an agent for intravascular administration for diagnostic and/or physiologic investigations, which agent consists of or contains a suspension of minute radioactive particles in a physiologically acceptable liquid.

Radioactively labelled microspheres, in suspension in a physiologically acceptable liquid, have lately been increasingly used in circulation studies, studies of the shunting phenomena, microcirculation studies, nutrition studies and as a means for carrying out scintography on man and animals.

2 Claims, No Drawings

AGENT FOR INTRAVASCULAR ADMINISTRATION

BACKGROUND

For the above-mentioned studies materials of two different types have been used, one type being particles which are not biologically degradable and the other type being particles which are biologically degradable i.e. which are degraded in vivo by enzymes occurring in the organisms. Usually the biologically degradable particles have been used in human experiments and the biologically non-degradable in animal experiments. One disadvantage common to these particles has been the problem with leakage of the radionuclide. To prevent this leakage attempts have been made to label the non-degradable particles already in connection with the production thereof so as to get an encapsulation of the radionuclide. These particles, which are made by i.a. different plastic materials, like carbonized ion-exchangers, have, however, several great disadvantages. They have a high density, which may cause sedimentation phenomena in the blood vessels. Also other rheologic disturbances may be caused by the high density, whereby the distribution of the particles in the blood capillaries may diverge in relation to the normal blood flow. Moreover, plastic particles in serum often aggregate, whereby further disorders may arise.

As the labelling with radionuclide is made in connection with the production of the carrier material, the product must be used immediately as radionuclides with a short half-life (5-60 days) are used almost exclusively within this field. The production of microspheres labelled with a radionuclide is very expensive and if it is not possible to use the material within a limited time after the production so that the radionuclide has decayed, great economic losses may occur. This will also limit the use of suitable radionuclides.

The degradable particles are usually labelled just before use. Hereby it has been possible to tolerate radionuclide labellings with low stability partly because of the fact that the microspheres have a limited in vivo life-time (due to the enzymatic degradation), partly because of the fact that generally radionuclides with a very short half-life have been used, which means that the choice of suitable radionuclides will be very limited. To make the use of more long-lived radionuclides possible without risking a deposition thereof in different organs, a stable and leakage-free binding of the radionuclide to the particles and also to the particle fragments obtained by the enzymatic degradation must be effected.

Also many of the proposed degradable particles, i.e. those based on denatured proteins, like albumin, have too high density and/or adhesitivity and may cause sedimentation and/or aggregation of the particles in the suspension. However, the particles known from Swedish patent application No. 7407461-8 do not have these mechanical disadvantages.

THE PRESENT INVENTION

According to the present invention it has been surprisingly discovered that a very stable binding of several different radionuclides to the particles used may be obtained without the particles suffering from the above-mentioned mechanical disadvantages.

The agent according to the present invention for intravascular administration for diagnostic and/or physiological investigations consists of or contains a suspension of minute particles in a physiologically acceptable liquid, which particles preferably have a particle size of 0.1-300 micrometer and are labelled with at least one metallic radionuclide, said particles being insoluble but swellable in water and comprising polymer molecules containing hydroxyl groups, preferably polymeric or polymerized carbohydrates or sugar-alcohols or physiologically acceptable derivatives thereof. This agent is mainly characterized in that said particles have covalently bound chelate-forming groups to which the radionuclide is bound in chelate complexes, which are mainly built up by at least four, preferably at least five to eight 5- or 6-membered rings, including the metal, and two metal coordinating atoms being located at a distance of two or three atoms from each other, one of the metal coordinating atoms being a nitrogen atom and the other a nitrogen atom or a sulphur atom or an oxygen atom, which oxygen atom is a part of a carboxylate-, sulphonate, or a phosphonate group or another equivalent negatively charged functional group.

The particles may preferably have at least two different chelate-forming groups to which the radionuclide is bound in chelate complexes consisting of at least four such 5- or 6-membered rings.

The term "chelate-forming groups" is intended to comprise such groups that together with metal ions give so-called chelate complexes with high stability constants.

The chelate-forming groups contain preferably at least three nitrogen atoms.

The chelate-forming groups may contain at least three sequences, which may be equal or different. In addition thereto certain atoms may be common to different sequences. These sequences may e.g. have the following formulae:

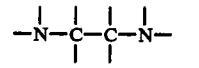

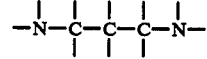

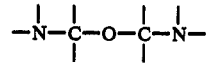

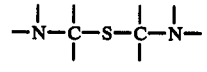

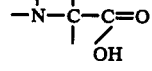

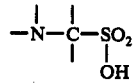

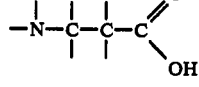

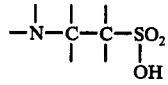

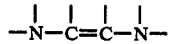

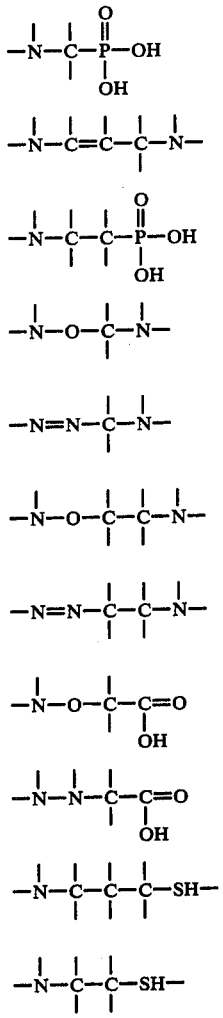
-continued

Also other sequences which contain a nitrogen atom and at a distance of two or three atoms from this nitrogen atom another nitrogen atom or a sulphur atom or an oxygen atom, said oxygen atom being part of a carboxylate-, sulphonate- or phosphonate group or another equivalent negatively charged functional group.

The chelate-forming groups may be covalently bound to hydroxyl groups in the polymer molecules by conventional methods for the introduction of substituents. Several of the conventional methods for binding of proteins and other substances to soluble and insoluble matrixes may be used for binding the chelate-forming groups to the matrix. The carboxyl groups in the chelate-former may for instance produce ester bonds to the carrier material by reaction in the presence of carbodiimides or other condensing reagents. On the other hand carboxyl groups may be introduced on the matrix and may be used to form amide bonds with the chelate-former. Reactive groups may be introduced on the polymer in different well-known ways and then accomplish a binding of the chelate-former by reaction with thiol or amino groups or other nucleophilic centra in the chelate-former. Examples on such groups are aldehyde and keto groups (partial oxidation of the matrix), halogenacetyl groups, azide groups, isocyanate and isothiocyanate groups, s-triazinyl groups, divinylsulphone groups, carbonic acid ester groups, imido carbonic acid ester groups (cyanogen bromide activation), oxirane groups and groups which easily are converted to oxirane derivatives and reactive disulphides. Dependent on the binding method chosen the complete chelate-former may be directly bound to the matrix or successively built by binding a starting material for the chelate-former to the matrix and thereafter chemically modifying the same.

Compounds with the general formula $H_2N[(CH_2)_n-NH]_m H$ where $n$ is 2 or 3 and $m$ is 1–100, may for example, be bound to the matrix and then be carboxymethylated or carboxyethylated more or less completely so that a chelate-former of the following type is obtained:

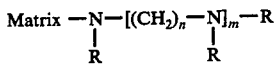
$$\text{Matrix} - \underset{R}{N} - [(CH_2)_n - \underset{R}{N}]_m - R$$

where R is H and/or $CH_2COOH$ and/or $CH_2CH_2COOH$.

The nitrogen-containing compound bound to the matrix contains in each case a certain number of nitrogen atoms $m + 1$, where $m$ preferably is 1–5, and it may be bound to the matrix at an arbitrary nitrogen. The number of carboxymethyl and/or carboxyethyl groups in each case may vary from 0 to $m + 2$. This leads to the generation of a very great number of different chelate-forming groups on the particles. In that way metals forming very stable chelates by simultaneous coordination to both the carboxyl groups and the nitrogen-containing groups, may preferably form such chelates, while metals forming more stable chelates with only nitrogen-containing groups may preferably form such chelates. Also chelates which have a composition between these types of chelates or where the hydroxyl groups of the matrix are included, are possible. Due to the presence of a series of different chelate forming groups one and the same particle will get a considerably widened use for different metals.

The above mentioned type of chelate-formers is only an exemplification of the groups which may be used in accordance with the invention. Thus the carboxymethyl and the carboxyethyl groups respectively may be replaced by sulphomethyl, sulphoethyl, phosphomethyl, respectively or phosphoethyl, aminoethyl respectively or aminopropyl or other equivalent groups. Besides chelate formers built up on analogous groups containing hydrazine or hydroxylamine may be used.

In order to give the metal matrix complex enough stability in vivo the metal ion used should be at least bivalent and should not belong to the groups alkali or alkaline-earth metals. The metal shall preferably be a transition metal, a lantanide or an aktinide.

The labelling with the metallic radionuclide is made in a very simple way be reacting a solution of a salt of the radionuclide with a suspension of the particles at room temperature, generally at a neutral or almost neutral pH (about pH 5–9). After the radionuclide has been fixed to the chelate former the suspension is suitably heated to about 80°–110° C. during a certain time. By this heating a stabilization of the metal complex is obtained.

The water-insoluble but swellable particles used in accordance with the invention may be non-degradable or biologically degradable particles and consist preferably of polymeric or polymerized carbohydrates or sugar-alcohols or physiologically acceptable derivatives thereof.

Especially the water-insoluble but swellable polymer particles consist of a hydroxyl group-containing three-dimensional net-work ketp together with bonds of a covalent character.

This three-dimensional net-work may preferably be obtained by cross-linking of the hydroxyl group-containing polymers, preferably polysaccharides or derivatives thereof, by bridges with bonds of a covalent character.

The cross-linking to the practically infinite three-dimensional net-work may be effected by reacting the hydroxyl-group containing polymers with an at least bifunctional cross-linking agent.

Preferably the polymer particles may consist of polysaccharides i.e. dextran, which have been cross-linked by bridges with bonds of a covalent character to a three-dimensional net-work which is insoluble but swellable in water, to which net-work polyamines have been bound, e.g. polyethyleneamines, which have been N-substituted in a varying degree with groups of the formula — $(CH_2)_n$ . COOH or — $(CH_2)_n$ $SO_2OH$, where $n$ is 1 or 2.

In order to obtain cross-linking bridges which are bound to the polymer chains, like the polysaccharide chains, over ether bonds, the hydroxyl group-containing polymer, e.g. the polysaccharide or the polysaccharide derivative, may be reacted, for example, in an alkaline aqueous solution with a cross-linking agent, for example of the type:

$$X . A_1 . Z \text{ (I) and } X . \overset{Y}{A_2} . Z \text{ (II)}$$

where X, Y and Z each represent a halogen atom, preferably chloro or bromo and $A_1$ and $A_2$ each represent a straight or branched aliphatic, saturated hydrocarbon chain which is substituted by one or more hydroxyl groups and preferably contains 3-30 carbon atoms, for example 3-20 carbon atoms, such as 3-10 carbon atoms and which is optionally broken by one or more oxygen atoms or with a corresponding epoxide compound which can be obtained from the compound (I) or (II) by splitting off a hydrogen halide. Examples of bifunctional substances of the formula $X . A_1 . Z$ and corresponding epoxide compounds which can be obtained from compounds of said formula by splitting off a hydrogen halide are:

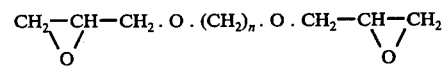

where n is an integer, for example from 2 to 4 and

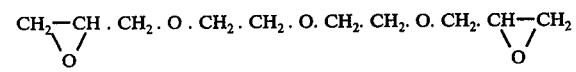
and

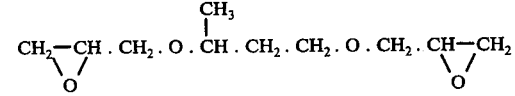
and

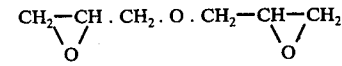
and

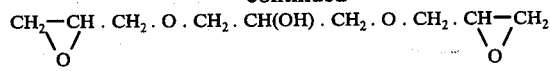

or corresponding halogen hydrins, and bifunctional glycerol derivatives of the formula $X . CH_2 . CH(OH) . CH_2 . Z$, for example, dichlorohydrin and dibromohydrin, or corresponding epoxide compound (obtainable by splitting-off a hydrogen halide) of the formula

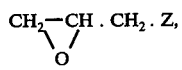

e.g. epichlorohydrin or epibromohydrin. Another example of such a bifunctional compound is 1,2 - 3,4-diepoxybutane of the formula

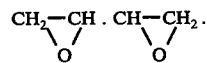

An example of a trifunctional cross-linking agent (which is an epoxide compound corresponding to a compound of the formula

is

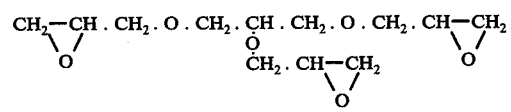

The polysaccharide or the polysaccharide derivative is reacted with such a quantity of an at least bifunctional cross-linking agent that a water-insoluble gel is formed, i.e. a practically infinite three-dimensional net-work which exhibits the desired properties. One skilled in this art can readily establish empirically a suitable relationship between the quantities of different polysaccharides or polysaccharide derivatives and cross-linking agent.

For the purpose of obtaining cross-linking bridges which are bound to the polysaccharide chains over ester bonds, the polysaccharide or the polysaccharide derivative can be reacted in a manner known per se with, for example, aliphatic or heterocyclic or aromatic dicarboxylic acids or reactive derivatives thereof, e.g. with dicarboxylic acid dichlorides (e.g. of succinic acid or of adipic acid) for example, with diisocyanates or diisothiocyanates. Other cross-linking agents may also be used.

The cross-linking reaction, in addition to bridge-building also often results in the introduction of monofunctionally bound (i.e. singly bound) substituents (mono-ethers, mono-esters etc.) from the cross-linking agent, i.e. only one reactive group in the art least bifunctional bridge-building agent has reacted with a hydroxyl group in a polysaccharide chain whilst the other reactive group or groups in the bridge-forming agent have e.g. instead reacted with, e.g. water to form, e.g. hydroxyl groups or carboxyl groups, etc. Consequently, the polymer product most frequently presents also monofunctionally bound substituents originating from the bridge-building agent; e.g. —O . $CH_2$ . CH(OH) .

$CH_2OH$ when the bridge-building agent is epichlorohydrin, and $-O \cdot CH_2 \cdot CH(OH) \cdot CH_2 \cdot O \cdot \cdot (CH_2)_4 \cdot O \cdot CH_2 \cdot CH(OH) \cdot CH_2OH$ when the bridge-building agent is 1,4-butandiol-diglycideether or, e.g. $-O \cdot CO \cdot (CH_2)_{n_1} \cdot COOH$ when the bridge-building agent is a dicarboxylic acid dichloride.

Among the non-degradable particles usable according to the invention such may be mentioned that are based on agarose and cross-linked agarose and cross-linked dextran and many other cross-linked polysaccharides and derivatives thereof. Also particles based on for example cross-linked polymerized saccharose or sorbitol may be advantageously used. Biologically degradable particles as used according to the invention may be based on cross-linked polysaccharides, like starch and glycogen and dextrines thereof degradable by α-amylase. The starch may thereby consist of amylase or amylopektin or mixtures thereof. Particles degradable by α-amylase are described in the Swedish patent application No. 7407461-8.

In both the case of degradable and non-degradable particles the cross-linked polysaccharide molecules in the three-dimensional net-work may be substituted with substituents other than the cross-linking bridges like in the above-mentioned Swedish patent application.

The polymer gel product may be obtained in formed pieces or in the form of particles either by preparing the polymerizates in the form of larger pieces (bulk polymerization) and then disintegrating them for example by grinding or by directly preparing the product by bead polymerization (dispersion polymerization) in the form of round particles. In the latter case the reaction mixture is dispersed to drops in an inert liquid immiscible therewith whereby the gel particles formed at the reaction in the drops are recovered. Preferably such particles having a spherical shape are chosen. By fractionation for example by sieving the desired particle sizes may be obtained.

The cross-linked polymer particles are insoluble in water (at least within the temperature range of 0° to 37° C.) but swell in water to gel particles. These gel particles may for example contain more than 50 percent by weight of water, preferably more than 65 percent by weight of water. It may, for example, contain less than 99.8 percent by weight of water, preferably less than 99.5 percent by weight of water. The particles in water-swollen state have suitably a density of 1.03–1.20, preferably of 1.05–1.15 g/cm$^3$. This will make them extraordinarily suitable for contact with blood, as the density of the red corpuscles is 1.098 g/cm$^3$. The particles may be of an irregular or spherical shape. Preferably a spherical shape is used.

The particles have preferably a particle size of 0.1–300 micrometer, for example 1–100 micrometer in a water-swollen state. Often particles of the size of 5–60 micrometer in a water-swollen state are chosen, when it is desired to block finer vessels.

The diagnostic agent is intended to be administered intravascularly i.e. preferably in blood vessels but sometimes also in lymphatic vessels.

The particle size may be so selected that the particles after intravascular administration will clog finer vessels in or leading to a certain portion of the body.

The particle size selected depends on the dimension of the vessels which are to be clogged. As an example of finer blood vessels of interest in this connection, blood capillaries of a diameter of 5–15 micrometer and meta arterioles with a diameter of about 15–300 micrometer may be mentioned. In certain cases, for example in the determination of the blood volumes with radioactive particles one may use so small particles that they do not even clog the finest blood capillaries.

After the intravascular administration the particles of the diagnostic agent, may clog the finer vessels whereby the flow in these vessels is retarded and the time of the radioactive substance in the vessel system is prolonged or its flow paths are diverted.

When the diagnostic agent is administered both the particles and the radionuclide will be delayed in the same vessel portion preferably upstreams of the finest vessels.

The diagnostic agent is administered in a quantity sufficient to give the desired effect in each case. The dosage of the agent (calculated per individual) is usually 0.1 to 2000 mg particles, e.g. 0.5 to 200 mg particles and is depending on the investigation to be effected, for instance which capillary area is to be investigated and possibly blocked. It may, for example, be 0.001 mg to 50 mg, preferably 0.01 mg to 25 mg, for example 0.05 mg to 10 mg particles per kilo of body weight.

The concentration of the particles in the suspension may be varied within wide limits, depending on the intended use. It may for instance be more than 0.01 mg, e.g. more than 0.1 mg, like more than 1 mg particles per 1 ml of suspension and for example less than 200 mg e.g. less than 50 mg, or less than 25 mg particles per 1 ml of suspension. The physiologically acceptable aqueous liquid wherein the particles have been suspended may be the usual fluids for intravascular injection, for example a saline solution (i.e. a 0.9 percent water solution of NaCl), or water solutions of glucose or sorbitol for example 5 percent water solutions, or solutions of the salts present in blood plasma, or also so-called plasma expanders. Other physiologically acceptable substances may be added to the suspension.

Preferably sterile suspensions of the particles are used. The sterilization may be effected by heating, for example by autoclaving or by adding substances, which prevent the growth of microorganisms. Aseptic preparation of suspensions may also be carried out.

The invention will be further illustrated by a number of concrete working examples.

EXAMPLE 1

To a suspension of 20 g particles of an epichlorihydrin cross-linked dextran gel with a swollen particle size of about 40–56 μm (Sephadex ® - G25 Superfine, from Pharmacia Fine Chemicals AB, Sweden), in 200 ml water, a solution of 24 g sodium hydroxide in 30 ml water was added whereafter 75 ml epichlorohydrin was added dropwise under stirring. The mixture was heated under continuous stirring in a vessel provided with a reflux condensor, to 60° C. for 2 hours. Initially a spontaneous temperature rise to reflux was obtained. The thus obtained epoxy derivative of the particles was washed on a filter with water to a neutral filtrate. The water was removed by washing with ethanol, dried and 65 g triethylene tetramine and 130 ml water was added. When adding water a sharp temperature rise was noticed. The mixture was stirred at room temperature for 48 hours whereafter the product was washed on a glass filter with water, 0.2 M hydrochloric acid and finally with water to a pH of 4–5. Samples were taken out and treated with 25 mM $CuSO_4$ whereby the gel particles became dark blue, which is typical for copper-amine complexes. The suspension was diluted with water to a total weight of 90 g, whereafter 16 g triethylamine and 10 g chloroacetic acid was added. The mixture was stirred at room temperature for 18 hours. The product was washed with water to a neutral pH and then with ethanol. Thereafter the product was dried. The nitrogen content of the product was 2.5 percent. By adding 25 mM CuSO$_4$ the product became intensely blue-green.

EXAMPLE 2

To 3 g of the epoxy derivative, prepared according to Example 1, 10 ml pentaethylenehexamine and 50 ml water was added. The mixture was stirred for 64 hours at room temperature. Then the gel particles were washed with 0.2 M hydrochloric acid, 2 M sodium hydroxide and water, whereafter the product was shrunk with acetone. The nitrogen content was 4.3 percent. The colour reaction with CuSO$_4$ gave the same result as in Example 1.

The carboxymethylation of 2 g of this product was carried out as in Example 1 by means of 3 g triethylamine and 1.8 g chloroacetic acid. The colour reaction with CuSO$_4$ gave the same result as in Example 1.

EXAMPLE 3

Polyehtyleneimine ($\overline{M}_w$ = 30.000-40.000) from Fluka AG, Switzerland was bound to an epoxy derivative, prepared according to Example 1 and carboxymethylated under conditions as indicated in Example 1 with the difference that the reaction mixture consisted of 2 g epoxy derivative, 10 ml 50 percent polyethyleneimine in water and 5 ml water. The nitrogen content was 5.1 percent. The colour reaction with CuSO$_4$ gave the same result as in Example 1.

EXAMPLE 4

According to known methods 3-chloro-2-hydroxypropyl groups were introduced (to a substitution degree of about 1 mmol/g) in a hydroxypropyl derivative of a cross-linked dextran gel (Sephadex ® - LH - 20, Pharmacia Fine Chemicals, Uppsala). To a suspension of 14 g of this derivative in 86 ml triethylenetetramine a solution of 2.9 g potassiumhydroxide in 120 ml methanol was added. The mixture was heated under stirring on a waterbath at 80° C. for 1 hour and thereafter at 55° C. for 2 hours. The product was washed on a filter with ethanol, water, ethanol and acetone and was finally suspended in benzene and dried in a rotation evaporator at 50° C. The nitrogen content was 6.7 percent. The product was carboxymethylated by refluxing 2 g of the substance in a mixture containing 10 ml benzene, 3 g triethylamine and 5 g ethylbromoacetate. IR-peak at 1740 cm$^{-1}$

Heating on a boiling waterbath with 2 M sodium hydroxide for 1 hour gave, after washing with water and ethanol and drying, a product with a strong IR-absorption at 1600 cm$^{-1}$

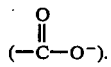

EXAMPLE 5

To 10 mg of the particles (40-56 μm) prepared according to Example 1 are provided with chelate forming groups 0.2 ml of a 0.5 M tris buffer (tris (hydroxymethyl)aminomethane/acetic acid, pH 8.8) was added. Thereafter 100μ Ci of $^{169}$YbCl$_3$ was added and the mixture was shaken for 1 hour. The particles were then carefully washed with the above-mentioned tris buffer. 0.1 ml of trisbuffer was added and the suspension was heated to 95° C. for 2 hours. 99–100 percent of the added $^{169}$Yb was bound to the particles.

Finally the particles were suspended in 2 ml of 0.9 percent saline-solution for injection in test animals and 0.2 ml of the suspension was injected in six guinea pigs by a catheter in the right heart ventricle. Three of the animals were killed after 5 minutes and the other three after 16 hours. The radioactivity as measured in the lungs of the test animals was 98–100 percent of the administrated activity for both of the experiment groups, which shows that no notable leakage of radioactivity in vivo had occurred after such a long time as 16 hours.

EXAMPLE 6

To 20 g of the epoxyderivative, prepared according to Example 1, 100 ml of bis-(3-aminopropyl)amine and 200 ml water was added. The mixture was stirred for 120 hours at room temperature, and then the gel particles were carefully washed with distilled water and shrunk with ethanol. 10 g of the product was mixed with 7.5 g triethylamine and 5 g of chloroacetic acid and 35 ml water. The reaction was allowed to proceed for 5.5 hours at 60° C. The product was washed with water (distilled twice) on a Büchner-funnel, shrunk with ethanol and finally vacuum dried at 40° C. over night. Nitrogen content: 1.4 percent. In vivo stability in mice lungs: loss of about 2 percent activity per hour of the two radionuclides $^{169}$Ytterbium and $^{57}$Cobalt. The test method was analogous to that used in Example 5 but the suspension of particles was injected into a tail vein. (It has been proved that the in vivo stability of chelate-complexes with metals, is lower in mice than in other mammals.)

EXAMPLE 7

The procedure in Example 6 was repeated but tris(2-aminoethyl)amine was used instead of bis(3-aminopropyl)amine. Nitrogen content of the product: 1.3 percent. In vivo stability in mice lungs: $^{169}$Ytterbium: loss of activity about 1 percent per hour. $^{57}$Cobalt: loss of activity: about 2 percent per hour. Metal binding capacity of the product:

| | |
|---|---|
| Mg$^{2+}$ | 22 μmol/g |
| Co$^{2+}$ | 130 μmol/g |
| Cu$^{2+}$ | 209 μmol/g |

EXAMPLE 8

The same procedure as in Example 6 was repeated but with the use of diethylenetriamine instead of bis(3-aminopropyl)amine. Nitrogen content of the product: 1.8 percent. In vivo stability in mice lungs: $^{169}$Ytterbium: loss of activity about 1 percent per hour. $^{58}$Cobalt: loss of activity about 1.5 percent per hour.

EXAMPLE 9

To 10 g of a product containing coupled triethylenetetramine, prepared according to Example 1 0.65 g acrylic acid and 5 ml water was added. The mixture was heated at 72° C. for 4 hours, whereafter the particles were carefully washed with distilled (twice) water and dried under vacuum. Nitrogen content of the product: 1.9 percent. In vivo stability in mice lungs: $^{169}$Ytterbium: loss of activity 5 percent per hour. $^{58}$Cobolt: loss of activity 3 percent per hour.

We claim:

1. An agent for intravascular administration for diagnostic and physiological investigations comprising a suspension of minute particles in a physiologically acceptable liquid, which particles have a particle size of 0.1–300 micrometer and are labelled with at least one metallic radionuclide, said particles being insoluble but swellable in water and comprising hydroxyl group-containing polymer molecules selected from the group consisting of polymeric and polymerized carbohydrates and sugar alcohols and physiologically acceptable derivatives thereof, wherein said particles are covalently bound to a chelate complex composed of at least four, 5-, or 6-membered rings, said complex including said radionuclide and two metal coordinating atoms at a distance of two or three atoms from each other, one of said metal coordinating atoms being a nitrogen atom and the other a nitrogen atom or a sulphur atom or an oxygen atom.

2. An agent according to claim 1 wherein the polymer molecules in the particles are crosslinked to a hydroxyl group containing three-dimensional net-work by bridges with bonds of a covalent character.

* * * * *